United States Patent
Bogild Hansen

(10) Patent No.: US 8,865,780 B2
(45) Date of Patent: Oct. 21, 2014

(54) PROCESS FOR CONVERTING BIOGAS TO A GAS RICH IN METHANE

(75) Inventor: John Bogild Hansen, Copenhagen Ø (DK)

(73) Assignee: Haldor Topsoe A/S, Lyngby (DK)

( * ) Notice: Subject to any disclaimer, the term of this patent is extended or adjusted under 35 U.S.C. 154(b) by 15 days.

(21) Appl. No.: 13/808,118

(22) PCT Filed: Jul. 9, 2010

(86) PCT No.: PCT/EP2010/004189
§ 371 (c)(1),
(2), (4) Date: Jan. 3, 2013

(87) PCT Pub. No.: WO2012/003849
PCT Pub. Date: Jan. 12, 2012

(65) Prior Publication Data
US 2013/0109767 A1    May 2, 2013

(51) Int. Cl.
C07C 27/00 (2006.01)
C25B 1/04 (2006.01)
C25B 3/04 (2006.01)
C07C 1/04 (2006.01)
C25B 1/02 (2006.01)
C01B 3/56 (2006.01)
C10L 3/08 (2006.01)

(52) U.S. Cl.
CPC ............. C07C 1/0485 (2013.01); C25B 1/04 (2013.01); Y02E 60/366 (2013.01); C25B 3/04 (2013.01); C01B 2203/042 (2013.01); C25B 1/02 (2013.01); Y02E 50/343 (2013.01); C01B 3/56 (2013.01); C01B 2203/0485 (2013.01); C10L 3/08 (2013.01)
USPC ............................ 518/700; 518/702; 518/704

(58) Field of Classification Search
USPC .......................................... 518/700, 702, 704
See application file for complete search history.

(56) References Cited

U.S. PATENT DOCUMENTS

| | | | |
|---|---|---|---|
| 4,298,694 A | | 11/1981 | Skov |
| 5,071,719 A | * | 12/1991 | Rostrup-Nielsen et al. .. 429/415 |
| 2004/0001994 A1 | * | 1/2004 | Marina et al. ................... 429/40 |
| 2004/0191595 A1 | * | 9/2004 | McElroy et al. ................ 429/21 |
| 2010/0162627 A1 | | 7/2010 | Clomburg, Jr. et al. |
| 2012/0178832 A1 | * | 7/2012 | Yogev et al. .................. 518/704 |

FOREIGN PATENT DOCUMENTS

WO    WO 2007/025280 A2    3/2007

OTHER PUBLICATIONS

JP abstract 62128901 Jul. 1987.*
J. Kopyscinski et al., "Production of Synthetic Natural Gas (SNG) from Coal and Dry Biomass—A Technology Review from 1950 to 2009," Fuel, vol. 89, No. 8, Feb. 6, 2010, pp. 1763-1783.
J.A. Mandler et al., "Control System Design for a Fixed-bed Methanation Reactor," Chemical Engineering Science, vol. 41, No. 6, 1986, pp. 1577-1597.
P. McKendry, "Energy Production from Biomass (part 2): Conversion Technologies," Bioresource Technology, vol. 83, No. 1, May 1, 2002, pp. 47-54.

* cited by examiner

Primary Examiner — Jafar Parsa
(74) Attorney, Agent, or Firm — Dickstein Shapiro LLP

(57) ABSTRACT

Process for converting biogas to a gas rich in methane comprising the steps of: —mixing a carbon dioxide-comprising biogas with steam to form a mixture comprising carbon dioxide, methane and steam; electrolysing the mixture comprising carbon dioxide, methane and steam in a high temperature solid oxide electrolyser cell unit, to obtain a gas comprising mainly hydrogen and carbon monoxide; catalytically converting hydrogen and carbon monoxide in the gas comprising hydrogen and carbon monoxide to methane in one or more methanation steps to obtain a gas rich in methane.

14 Claims, 4 Drawing Sheets

PROCESS FOR CONVERTING BIOGAS TO A GAS RICH IN METHANE

The invention concerns a process for converting biogas to a gas rich in methane. In particular the invention concerns a process for upgrading biogas to substitute natural gas (SNG) by means of high temperature SOEC electrolysis and SNG technology.

Biogas obtained from conversion of biomass represents a potential source of energy from renewables which could cover a percentage of the total energy consumption on a global level. There are several end use options including combined heat and power (CHP) and compressed methane (NG) for vehicle use. However the cost involved per $Nm^3$ appears to be prohibitive. Amongst these options attention has been given to upgrade biogas to pipeline quality by removing the main part of the carbon dioxide in the biogas.

Biogas is obtainable from for example municipal waste, sewage water, grass and livestock manure and are suitable as resources for green energy purposes. It consists typically of 60% methane and 40% $CO_2$ and contains sulphur in amounts typically around 1000 ppm. In addition the sulphur content in biogas which is currently brought down by biological removal or other methods.

Examples of current methods for converting biogas into energy are summarised in the following disclosures. These methods primarily utilise the methane content of desulphurised biogas in fuel cells for energy generation. Other methods include reforming of the methane obtained from biogas to synthesis gas for utilisation of the obtained hydrogen in fuel cells.

The conversion of gaseous or gasifiable fuels with high methane content, such as natural gas or biogas originated from various industrial process rejects to light hydrocarbons, primarily ethylene and ethane, is known.

WO patent application no. 010000049 discloses a process whereby such fuels, with or without prior desulfurization and elimination of other contaminants, are converted in a solid oxide fuel cell (SOFC), with special anodes, based on mixed oxides or metal oxides with a perovskite type structure, either or not nanostructured, into $C_2$ hydrocarbons by oxidative coupling of methane.

US patent application no. 2007029264 discloses generation of a biogas which contains methane. The biogas is supplied to a catalytic reformer unit to form a synthesis gas; steam may also be supplied, and the proportion of steam to methane is adjustable so that the synthesis gas may be rich in hydrogen or alternatively rich in carbon monoxide. Adjusting the proportion of steam to biogas enables the output of the process to be adjusted according to market conditions. If the synthesis gas is rich in hydrogen, it may be supplied to a fuel cell to generate electricity, while if it is rich in carbon monoxide, it may be used to generate liquid hydrocarbons in a Fischer-Tropsch synthesis reactor.

JP patent application no. 2005330334 discloses a fuel gas supply apparatus which uses a biogas obtainable from organic wastes and includes a desulfurizer that removes hydrogen sulfide, a purification tower that removes various impurities, a methane gas concentration apparatus that concentrates the methane gas, and a gas tank, wherein the obtained gas is supplied to a plurality of fuel cell power generators and the gas tank is provided with an auxiliary fuel gas supply circuit to compensate a deficient supply of the biogas with the auxiliary fuel gas.

JP patent application no. 2003277779 discloses a process whereby a biogas having sulfur compounds removed therefrom at a high efficiency, is used as a fuel for a solid oxide electrolyte fuel cell. A biogas containing sulfur compounds, obtained by subjecting an organic substance to methane fermentation is sent to a desulfurizer. An adsorbent comprising an iron-base adsorbent is used in the desulfurizer, so that hydrogen sulfide in the sulfur compounds is desulfurized therein. An adsorbent comprising a zeolite-base adsorbent is used in a highly desulfurizing unit, so that sulfur compounds such as methyl sulfide and methyl mercaptan, which have not been removed in the iron-based desulfurizer, are desulfurized therein. A biogas having sulfur compounds completely desulfurized is fed to a fuel cell. The performance of the fuel cell can be maintained by using the biogas having sulfur compounds thus removed.

DE patent application no. 10113879 discloses an energy generation system whereby biogas generated by fermentation of organic wastes from agriculture, sewage processing, food processing or fermentation of plants grown for this purpose, is especially converted to electrical energy by an MCFC carbonate fusion fuel cell. The energy generation system includes a fermenting tank, gas holder, integrated reformer, gas filter, gas mixer, heat exchanger and fuel cell. In addition to containing trace elements, the biogas comprises methane and carbon dioxide. The $CO_2$ content is preferably 25-50 percent by volume. The ammonia content is preferably 10-30 percent by volume and is derived from biogas generation residues. The ammonia gas is generated by stripping biogas foul sludge. Prior to its use in the fuel cell, harmful trace elements, especially hydrogen sulfide, are removed from the gas which then passes through an integrated reformer unit.

The above-mentioned methods deal primarily with utilisation of methane and removal of sulphur from methane in biogas. Biogas contains approximately 60% methane, the methane representing an important contribution to the greenhouse effect as it has a much stronger greenhouse effect than carbon dioxide.

There is therefore a need for a process whereby biogas is treated to obtain pipeline quality and having reduced contribution to the green house effect, as the biogas then ultimately will be converted to carbon dioxide while providing useful energy services.

The objective of the invention is to provide a process whereby biogas is upgraded to pipeline quality by converting biogas to a gas rich in methane suitable for addition to or replacement of natural gas in the pipeline.

This objective is achieved by providing a process for converting biogas to a gas rich in methane comprising the steps of:
  mixing a carbon dioxide-comprising biogas with steam to form a mixture comprising carbon dioxide, biogas and steam;
  electrolysing the mixture comprising carbon dioxide, biogas and steam in a high temperature solid oxide electrolyser cell unit, to obtain a gas comprising hydrogen and carbon monoxide;
  catalytically converting hydrogen and carbon monoxide in the gas comprising hydrogen and carbon monoxide to methane in one or more methanation steps to obtain a gas rich in methane.

The invention also includes a system for converting biogas to a gas rich in methane, the system comprising:
  optionally a digester or a fermenter for formation of biogas from biomass
  a high temperature solid oxide electrolyser cell unit in series with one or more methanation reactors located downstream the solid electrolyser cell unit, the methanation reactor immediately downstream the high temperature solid oxide electrolyser cell unit being at least one adiabatic reactor, and a non-adiabatic methanation reactor located downstream the at least one adiabatic reactor means for regulating the temperature of the process gas prior to, after and between the solid electrolyser cell unit and the methanation reactors.

The process of the invention has the following features:

1. Process for converting biogas to a gas rich in methane comprising the steps of:
   mixing a carbon dioxide-comprising biogas with steam to form a mixture comprising carbon dioxide, methane and steam;
   electrolysing the mixture comprising carbon dioxide, methane and steam in a high temperature solid oxide electrolyser cell unit, to obtain a gas comprising mainly hydrogen and carbon monoxide;
   catalytically converting hydrogen and carbon monoxide in the gas comprising hydrogen and carbon monoxide to methane in one or more methanation steps to obtain a gas rich in methane.
2. Process according to feature 1, wherein the mixture comprising carbon dioxide, biogas and steam also comprises a sulphide compound which is present during electrolysis.
3. Process according to anyone of features 1 or 2, wherein the mixture comprising carbon dioxide, biogas and steam also comprises approximately 0.1-500 ppm of sulphide compound.
4. Process according to anyone of features 1-3, wherein the gas comprising hydrogen and carbon monoxide is desulphurised after electrolysis and prior to methanation.
5. Process according to anyone of features 1 to 4, wherein the mixture comprising biogas, carbon dioxide and steam is co-electrolysed according to the following reactions:

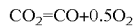

$$CO_2 = CO + 0.5 O_2 \quad (1)$$

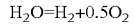

$$H_2O = H_2 + 0.5 O_2 \quad (2)$$

6. Process according to anyone of features 1 to 5, wherein the high temperature solid oxide electrolyser cell unit comprises fuel electrode material with limited steam reforming activity or without steam reforming activity.
7. Process according to feature 6, wherein the fuel electrode material does not comprise nickel or the fuel electrode material is all ceramic.
8. Process according to feature 6, wherein the fuel electrode material comprises compounds or elements selected from the group consisting of LSCM, Cu, $CeO_2$, titanates and combinations thereof.
9. Process according to feature 6, wherein the fuel electrode material comprises Ni-YSZ, SYSZ or Ni-SSZ electrodes having a thickness of less than or equal to 10 microns.
10. Process according to anyone of the previous features, wherein the high temperature solid oxide electrolyser cell unit operates thermoneutrally.
11. Process according to anyone of features 2 to 4, wherein the sulphide is removed from the hydrogen-rich gas by absorption on a metal oxide absorbent.
12. Process according to feature 11, wherein the metal oxide absorbent is zinc oxide and/or is based on copper.
13. Process according to anyone of features 1 to 12, wherein carbon monoxide and hydrogen are converted to methane in a methanation step according to the following reactions:

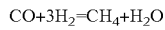

$$CO + 3H_2 = CH_4 + H_2O \quad (3)$$

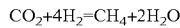

$$CO_2 + 4H_2 = CH_4 + 2H_2O \quad (4)$$

14. Process according to anyone of features 1 to 13, wherein the one or more methanation steps are catalysed by a catalyst including metals selected from the group consisting of Group 6B, Group 8 of the Periodic Table and combinations thereof. Preferably the catalyst is selected from Group 8 or combinations of Group 8 and 6B, for instance a nickel based catalyst. Commercially available catalysts from Haldor Topsøe A/S such as MCR and PK7(R) are suitable.
15. Process according to anyone of features 1 to 14, wherein the carbon-dioxide comprising biogas comprises methane. Typically the biogas can comprise up to 60 mol % methane and 40 mol % carbon dioxide. The biogas is obtainable by for instance anaerobic digestion of biomass in a digester.
16. Process according to anyone of the previous features, wherein the one or more methanation steps include adiabatic methanation followed by non-adiabatic methanation. Adiabatic methanation is carried out in an adiabatic reactor and non-adiabatic methanation is carried out in a reactor where the temperature is controlled, such as a boiling water reactor.
17. System for converting biogas to a gas rich in methane, the system comprising:
   optionally a digester for formation of biogas from biomass
   a high temperature solid oxide electrolyser cell unit in series with one or more methanation reactors located downstream the solid electrolyser cell unit, the methanation reactor immediately downstream the high temperature solid oxide electrolyser cell unit being at least one adiabatic reactor, and a non-adiabatic methanation reactor located downstream the at least one adiabatic reactor
   means for regulating the temperature and pressure of the process gas prior to, after and between the solid electrolyser cell unit and the methanation reactors.

Figure 1:
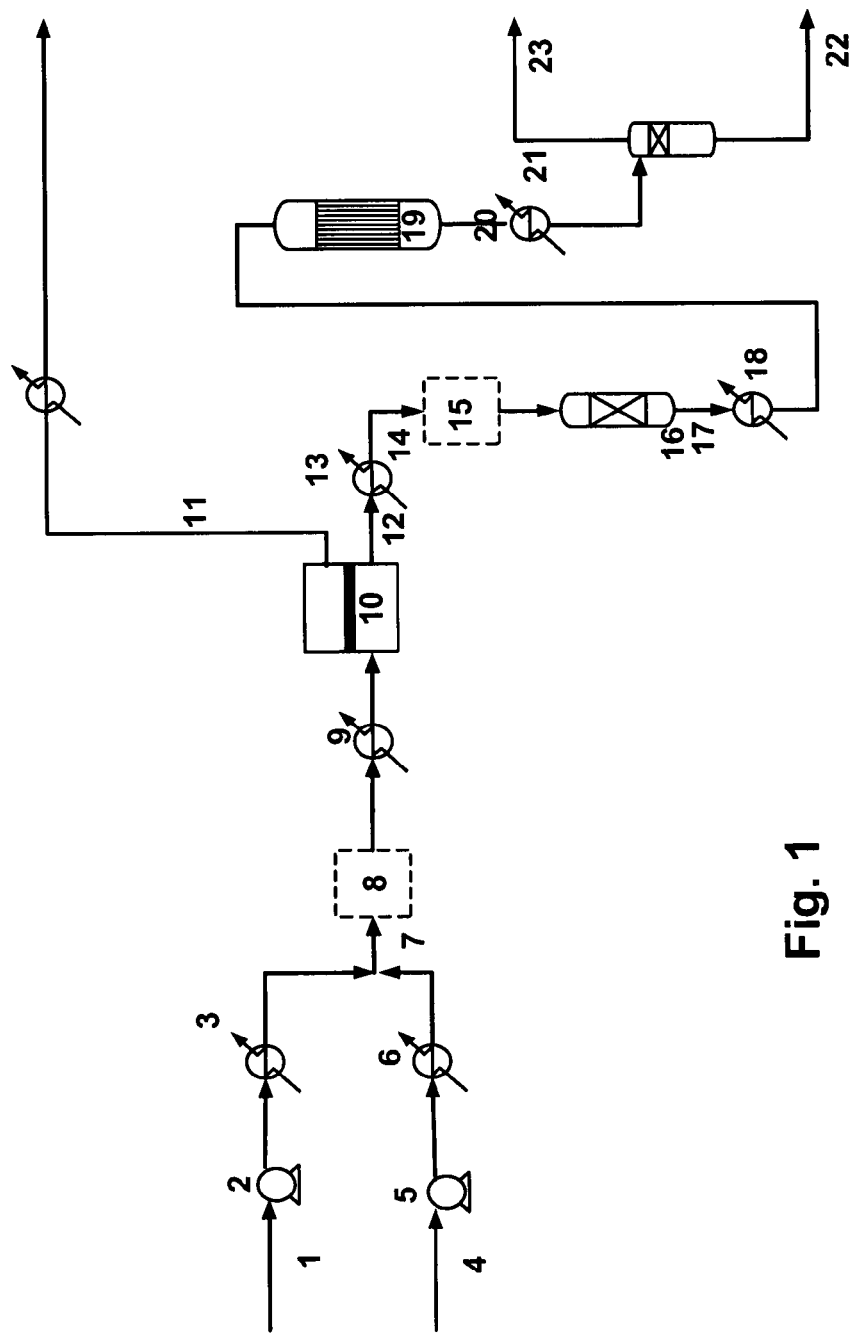
FIG. 1 illustrates the process of the invention.

The high temperature solid oxide electrolyser cell unit is defined as having one or more solid oxide electrolyser cell stacks comprising a plurality of solid oxide electrolyser cells and the means required for operating the stack.

High temperature SOEC electrolysis of carbon dioxide and water occurs at temperatures typically between 500 to 1000° C.

In the SOEC stack co-electrolysis of carbon dioxide present in biogas and of steam takes place according to reactions (1) and (2) respectively:

$$CO_2 = CO + 0.5 O_2 \quad (1)$$

$$H_2O = H_2 + 0.5 O_2 \quad (2)$$

The electrolysis of one mole of $CO_2$ results in the formation of 1 mole of carbon monoxide and ½ mole of oxygen. The electrolysis of 1 mole of $H_2O$ results in the formation of 1 mole of carbon monoxide and ½ mole of oxygen. A stoichiometric gas comprising hydrogen and carbon monoxide with respect to methanation is obtained.

Operating pressures for the inventive process are equal to or more than 2 bar gauge. The maximum pressure is 80 bar gauge corresponding to pipeline pressure. Preferably the process pressure is from 2-20 bar gauge, and most preferably the pressure is 4-8 bar gauge.

It is an advantage if the SOEC unit is situated at the location of the biomass digester, as the oxygen generated during electrolysis is suitable for use in the digester to gasify the biomass.

It is a further advantage if the methanator used is a boiling water reactor, as the steam generated can be used in the electrolysis step.

The product obtained by the process of the invention is a gas rich in methane. The product gas comprises at least 95% methane.

Reactions (1) and (2) are strongly endothermic but electrolysis can be operated thermoneutrally by adjusting the voltage for each of the two reactions according to equation (3) below:

$$E_{Tn} \equiv \frac{\Delta H_f}{nF} = \frac{\Delta G_f}{nF} + \frac{T\Delta S_f}{nF}$$

However operation using conventional fuel electrodes comprising nickel will lead to considerable cooling of the stack due to activity for internal steam reforming within the stack according to equation (4), which is an endothermic reaction:

$$CH_4 + H_2O = CO + 3H_2 \quad (4)$$

Considerable cooling of the stack results in unacceptable performance during operation of the stack. Furthermore it is not desirable to reduce the methane content which also requires supplying heat to this endothermic process in the form of electricity. Additionally the ensuing methanation step is exothermic and thus also releases heat, which will then be in surplus.

This problem can be solved by reducing the reforming activity using a fuel electrode with very limited reforming activity or no reforming activity. Examples of such fuel electrodes are electrodes not comprising nickel or comprising nickel in limited amounts, or all ceramic fuel electrodes.

Examples of fuel electrode materials are:
    fuel electrode material comprising compounds or elements selected from the group consisting of LSCM, Cu, $CeO_2$, titanates and combinations thereof.
    fuel electrode material comprising nickel and yttria stabilised zirconia (Ni-YSZ), strontium and yttria stabilised zirconia (SYSZ) or nickel and strontium stabilised zirconia (Ni-SSZ) electrodes having a thickness of less than or equal to 10 microns.

The carbon dioxide comprising biogas may also contain a sulphide compound for instance in the form of hydrogen sulphide, $H_2S$. The presence of a sulphide is desirable as it chemisorps on the nickel present in the fuel electrode. This results in a strong reduction of the fuel electrode's activity for steam reforming.

The carbon dioxide comprising-biogas may comprise a sulphide compound, which may already be present in the biogas from the biomass or it may be deliberately added to the carbon dioxide comprising-biogas. It is preferable that the sulphide compound is present in an amount of 0.1-200 ppm, as this allows regulation by the ZnO bed. It is more preferable that the sulphide compound is present in an amount of 1 ppm.

The amount of hydrogen sulphide is a compromise between strongly reducing the steam reforming activity while at the same time not reducing the electrochemical activity for electrolysis.

Hydrogen may also be added to the carbon dioxide and sulphur comprising-biogas in order to form $H_2S$ which can be equilibrated over for instance ZnO at 250-450° C. to provide the required amount of $H_2S$ (0.1-500 ppm) prior to entering the SOEC unit. After electrolysis and prior to adiabatic methanation, the obtained gas comprising hydrogen and carbon monoxide is finally desulphurised, if necessary, in for instance a ZnO bed and optionally a Cu guard bed operating from 250-350° C.

In still another embodiment of the invention, hydrogen is provided to the SOEC stack by means of a recycle of (product) gas comprising mainly hydrogen and carbon monoxide from the SOEC stack. This gas is split into two streams cooling. The minor part is recycled by means of an ejector which uses steam (reactant) as motive force.

Alternatively the gas comprising mainly hydrogen and carbon monoxide is recycled to the SOEC by adding it to the mixture comprising carbon dioxide, methane and steam, optionally heating the combined mixture and recycle gas prior to entering the SOEC.

In another embodiment of the invention, hydrogen is provided to the SOEC stack (main SOEC stack) by means of a small additional SOEC stack producing hydrogen from steam according to reaction (2). The stream of steam (reactant) after preheating in an exchanger is split in two streams. The minor stream is further preheated in another exchanger to the inlet temperature, typically around 800° C., of the SOEC stack where part of the steam is electrolysed to hydrogen. The hydrogen comprising stream is then sent to the main SOEC stack.

Equilibrating the hydrogen sulphide content at e.g. 340 C results in a hydrogen sulphide content of 1 ppm, corresponding to 90% of the nickel surface in the fuel electrode being covered by sulphur. It is preferable that 90-95% of the nickel surface is covered by sulphur, because this gives a good compromise between steam reforming and electrochemical activity. This figure can also be expressed as theta S:

$$\theta s = 0.90 - 0.95.$$

An embodiment of the process of the invention is illustrated in FIG. 1.

A carbon dioxide and methane comprising biogas 1, which may also contain a sulphide compound, is compressed by compressor 2 to the desired operating pressure and preheated in exchanger 3. Water 4 is compressed by pump 5, evaporated and preheated in exchanger 6 and then mixed with the preheated, compressed biogas. The combined stream of biogas and steam, 7, is then desulfurised to the desired content of sulphide compound in the desulphuriser 8. The desired level of sulphur content is obtained by adjusting the operating temperature of the desulphuriser. The mixture is further preheated in exchanger 8 to the required inlet temperature of the solid oxide electrolysis cell (SOEC) stack(s) 10, which is typically around 800° C. In the SOEC stack, 10, co-electrolysis of carbon dioxide present in the biogas, 1, and of steam from stream, 2, takes place according to reactions (1) and (2)

$$CO_2 = CO + 0.5O_2 \quad (1)$$

$$H_2O = H_2 + 0.5O_2 \quad (2)$$

The SOEC stack may be operated at approximately 1.33 V, close to thermoneutral conditions. The exit gas, 12, is cooled down in exchanger 13 to for instance 300° C., and if a sulphide is present then the gas comprising hydrogen and carbon monoxide, 14, may be desulphurised in a ZnO bed 15 optionally with a Cu guard and then sent to the adiabatic methanation reactor, 16, for conversion of the hydrogen and carbon monoxide to a gas with an increased amount of methane, 17. One or more extra methanation steps may be carried out using at least one adiabatic reactor.

The amount of methane present in the gas with increased amount of methane, 17, is further increased by including a methanation step in a temperature controlled methanator, 19, such as a boiling water reactor. The gas obtained, 20, from that reactor contains methane and water and small amounts of hydrogen, carbon monoxide and carbon dioxide. After cooling of the gas in exchanger 20, water 22, is removed and a gas rich in methane, 23, is obtained which is suitable as substitute natural gas (SNG) and be compressed to the pipeline. The operating pressure, typically around 6 bar g, and the temperature of the final methanator, typically around 280° C., are adjusted to meet the pipeline quality required with respect to methane content and residual amounts of carbon monoxide and carbon dioxide. Another oxygen rich stream 24 is also produced in the SOEC in the plant and can be delivered for oxygen consuming processes.

Intermediate regulation of the temperature or pressure of the reactants may be carried out between some or all the reaction steps in order to ensure optimal reaction conditions at each step.

The steam in stream 7 may be wholly or partially generated in the methanator, 19, and by utilising the heat available in heat exchangers 13, 18 and 21. This heat may also be used for preheat of the biogas, 1, and the feed preheater, 9, to the SOEC. Final temperature adjustment in, 9, may be carried out by means of electricity or a high temperature heat source.

Figure 2:
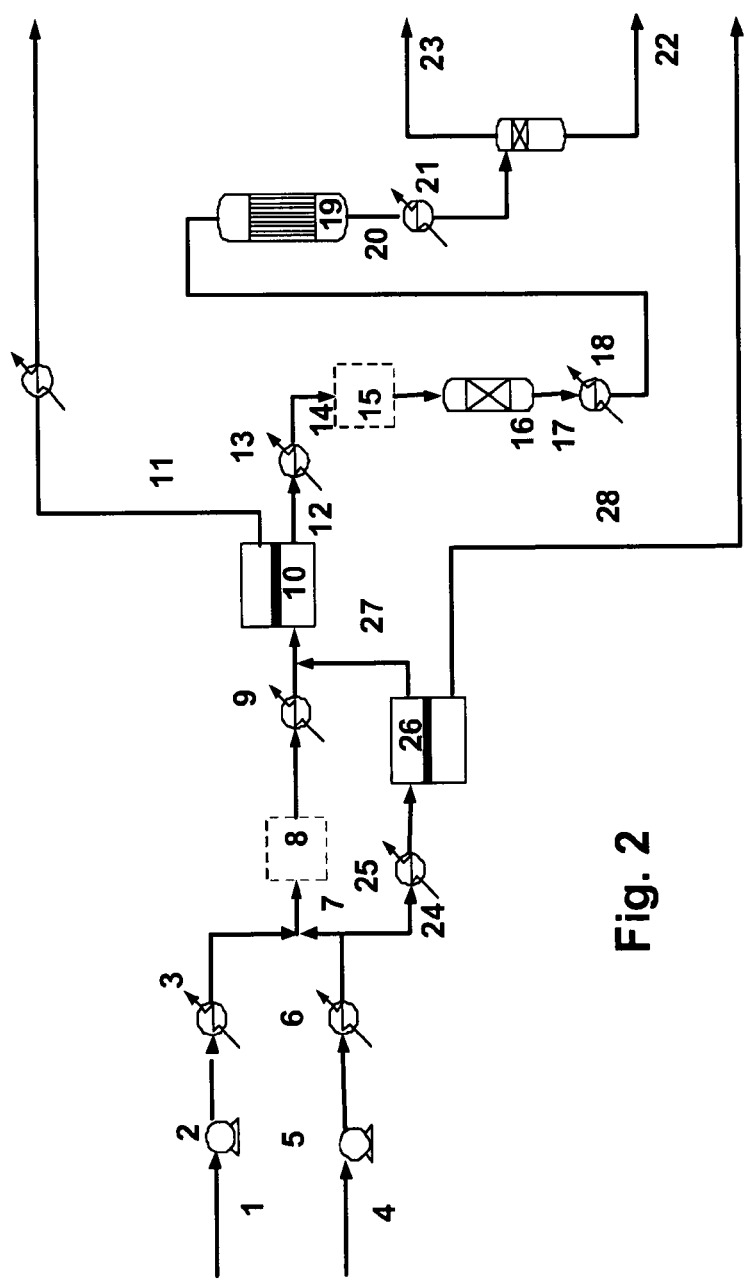
FIG. 2 illustrates the provision of hydrogen to the stack in an embodiment of the invention.

In another embodiment of the invention, shown on FIG. 2, hydrogen is provided to the SOEC stack by means of a small SOEC stack producing hydrogen from steam according to reaction (2). The stream of steam after preheating in exchanger is split in two streams. The minor stream, 24, is further preheated in exchanger 25 to the inlet temperature, typically around 800° C., of the SOEC stack 26 where part of the steam is electrolysed to hydrogen. The hydrogen comprising stream 27 is then sent to the SOEC stack 10.

Figure 3:
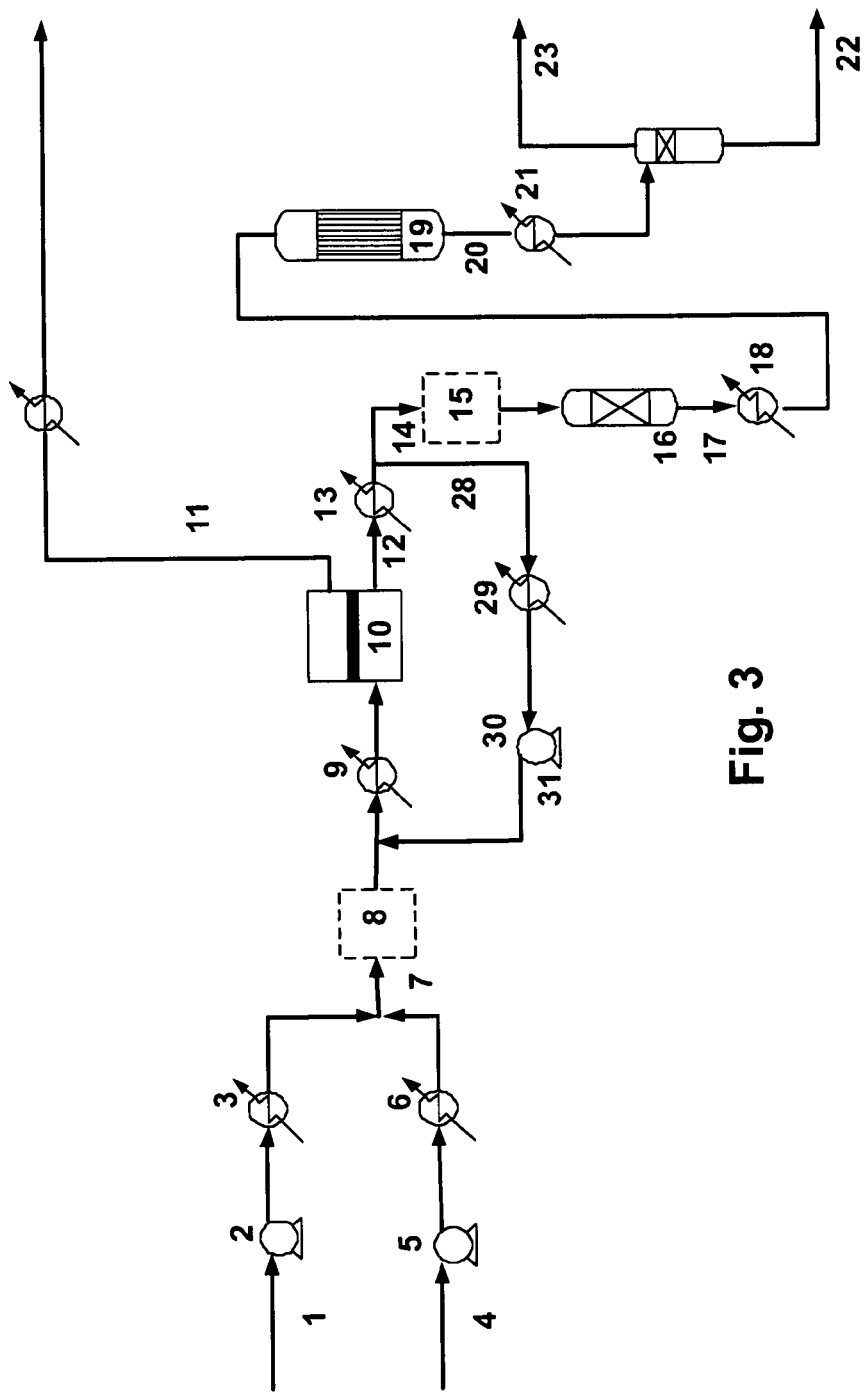
FIG. 3 illustrates the provision of hydrogen to the stack in another embodiment of the invention.

In another embodiment of the invention, shown on FIG. 3, hydrogen is provided to the SOEC stack by means of a recycle of product gas from the SOEC stack 10. The stream 12 is split into two streams 14 and 28 after the cooler 13. The minor part 28 is further cooled to the inlet temperature of the compressor 30 and is returned upstream the SOEC stack preheater as stream 31.

Figure 4:
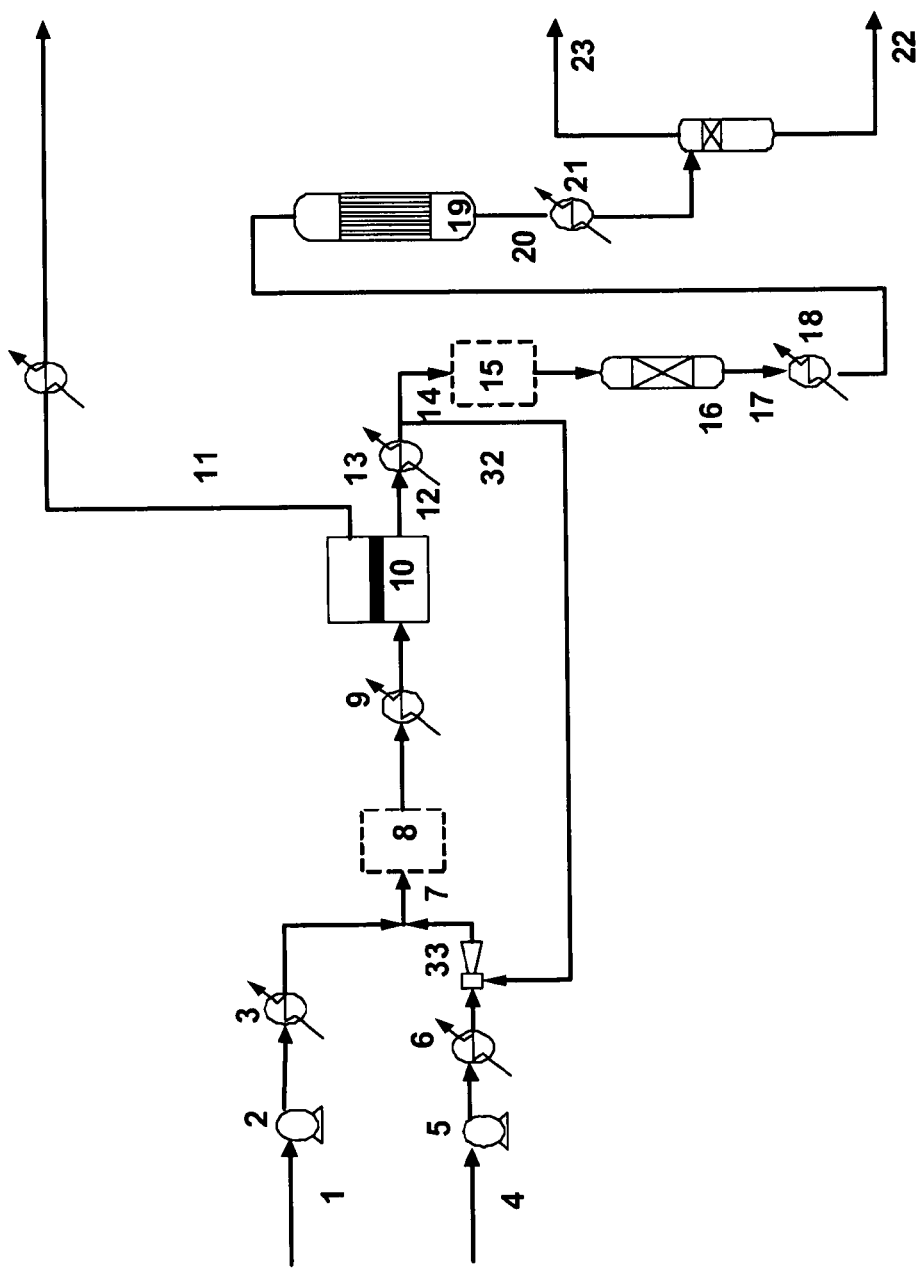
FIG. 4 illustrates the provision of hydrogen to the stack in yet another embodiment of the invention.

In still another embodiment of the invention, shown on FIG. 4, hydrogen is provided to the SOEC stack by means of a recycle of product gas from the SOEC stack 10. The stream 12 is split into two stream 14 and 32 after the cooler 13. The minor part 32 is recycled by means of the ejector 33 which is using steam from exchanger 6 as motive force.

In FIGS. 3-4 the hydrogen is supplied to the SOEC stack in the amount of 0.1-10 mole %, preferably around 1 mole %. This content of hydrogen will prevent bulk suphidation occurring on a nickel containing-fuel electrode according to equation (5):

$$Ni+H_2S=Ni_3S_2+2H_2 \quad (5)$$

This reaction would be very detrimental as $Ni_3S_2$ melts at 789° C.

EXAMPLE

This example illustrates the process of the invention as shown in FIG. 1. Table 1 shows the operation conditions and gas compositions of the various streams in FIG. 1.

| Stream Number | 1 | 4 | 7 | 12 | 23 | 22 |
|---|---|---|---|---|---|---|
| Temperature (° C.) | 40 | 20 | 825 | 819 | 20 | 20 |
| Pressure (bar g) | 0.01 | 0 | 5.85 | 5.85 | 5.7 | 5.7 |
| Total Flow (kmol/h) | 2.68 | 3.48 | 6.16 | 6.2 | 2.76 | 1.36 |
| Mass Flow (kg/h) | 72.89 | 62.69 | 135.58 | 69.27 | 44.72 | 24.56 |
| Composition (Mole %) | | | | | | |
| H2O | | 100 | 56.52 | 4.72 | 0.35 | 99.98 |
| H$_2$ | | 0 | 0 | 52.1 | 2.56 | 0 |
| CO | | 0 | 0 | 16.12 | 0 | |
| CO$_2$ | 40 | 0 | 17.39 | 1.49 | 1.89 | 0.01 |
| CH$_4$ | 60 | 0 | 26.09 | 25.57 | 95.2 | 0.02 |
| O$_2$ | | | | | | |
| Mole Weight (kg/kmol) | 27.23 | 18.02 | 22.02 | 11.18 | 16.22 | 18.02 |

The invention claimed is:

1. Process for converting biogas to a gas rich in methane comprising the steps of:
   mixing a carbon dioxide-comprising biogas with steam to form a mixture comprising carbon dioxide, methane and steam;
   electrolysing the mixture comprising carbon dioxide, methane and steam in a high temperature solid oxide electrolyser cell unit, to obtain a gas comprising mainly hydrogen and carbon monoxide; and
   catalytically converting hydrogen and carbon monoxide in the gas comprising hydrogen and carbon monoxide to methane in one or more methanation steps to obtain a gas rich in methane.

2. Process according to claim 1, wherein the one or more methanation steps include adiabatic methanation followed by non-adiabatic methanation.

3. Process according to claim 1, wherein the mixture comprising carbon dioxide, biogas and steam also comprises approximately 0.1-200 ppm of sulphide compound.

4. Process according to claim 1, wherein the gas comprising hydrogen and carbon monoxide is desulphurised after electrolysis and prior to methanation.

5. Process according to claim 1, wherein the mixture comprising biogas, carbon dioxide and steam is co-electrolysed according to the following reactions:

$$CO_2=CO+0.5O_2 \quad (1)$$

$$H_2O=H_2+0.5O_2 \quad (2).$$

6. Process according to claim 1, wherein the high temperature solid oxide electrolyser cell unit comprises fuel electrode material with limited or no steam reforming activity.

7. Process according to claim 6, wherein the fuel electrode material does not comprise nickel or the fuel electrode material is all ceramic.

8. Process according to claim 6, wherein the fuel electrode material comprises compounds or elements selected from the group consisting of LSCM, Cu, CeO$_2$, titanates and combinations thereof.

9. Process according to claim 6, wherein the fuel electrode material comprises Ni-YSZ, SYSZ or Ni-SSZ electrodes having a thickness of less than or equal to 10 microns.

10. Process according to claim 1, wherein the high temperature solid oxide electrolyser cell unit operates thermoneutrally.

11. Process according to claim 2, wherein the sulphide is removed from the hydrogen-rich gas by absorption on a metal oxide absorbent.

12. Process according to claim 11, wherein the metal oxide absorbent is zinc oxide and/or is based on copper.

13. Process according to claim 1, wherein carbon monoxide and hydrogen are converted to methane in a methanation step according to the following reactions:

$$CO + 3H_2 = CH_4 + H_2O \quad (3)$$

$$CO_2 + 4H_2 = CH_4 + 2H_2O \quad (4).$$

14. Process according to claim 1, wherein the one or more methanation steps are catalysed by a catalyst including metals selected from the group consisting of Group 6B, Group 8 of the Periodic Table and combinations thereof.

* * * * *